United States Patent
Chen et al.

(10) Patent No.: US 12,092,561 B2
(45) Date of Patent: Sep. 17, 2024

(54) REAGENT, METHOD FOR ANALYZING PLATELETS AND BLOOD CELL ANALYZER

(71) Applicant: Shenzhen Mindray Bio-Medical Electronics Co., Ltd., Shenzhen (CN)

(72) Inventors: Gengwen Chen, Shenzhen (CN); Ziqian Zhang, Shenzhen (CN); Yi Ye, Shenzhen (CN); Zhaoyang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 772 days.

(21) Appl. No.: 17/081,712

(22) Filed: Oct. 27, 2020

(65) Prior Publication Data
US 2021/0041341 A1 Feb. 11, 2021

Related U.S. Application Data

(63) Continuation of application No. PCT/CN2019/084648, filed on Apr. 26, 2019.

(30) Foreign Application Priority Data

Apr. 28, 2018 (CN) .......................... 201810402750.X

(51) Int. Cl.
*G01N 15/00* (2024.01)
*G01N 15/14* (2006.01)
(Continued)

(52) U.S. Cl.
CPC ....... *G01N 15/147* (2013.01); *G01N 33/5094* (2013.01); *G01N 2015/011* (2024.01); *G01N 2015/012* (2024.01); *G01N 2015/018* (2024.01)

(58) Field of Classification Search
CPC ....... G01N 33/5094; G01N 2015/0069; G01N 2015/008
See application file for complete search history.

(56) References Cited

U.S. PATENT DOCUMENTS

| 4,336,029 A | 6/1982 | Natale |
| 9,329,172 B2 * | 5/2016 | Kimura ............. G01N 33/5094 |

(Continued)

FOREIGN PATENT DOCUMENTS

| CN | 101173921 A | 5/2008 |
| CN | 101490547 A | 7/2009 |

(Continued)

OTHER PUBLICATIONS

"Live Cell Stains for Microscospy" Biotum webstie, Sep. 29, 2017.*

*Primary Examiner* — Rebecca C Bryant
(74) *Attorney, Agent, or Firm* — Kory D. Christensen

(57) ABSTRACT

A reagent, a method for differentiating platelets under a hemolysis condition using the reagent and a blood cell analyzer are provided. The reagent includes a first reagent as a hemolytic agent, and a second reagent which is a membrane-specific dye or a mitochondrion-specific dye. By using the reagent, the method and the blood cell analyzer, platelets can be differentiated and an alarm about reticulocytes can be provided under a hemolysis condition, and white blood cell can further be classified and counted, thereby quickly and accurately analyzing a blood sample in a single channel.

22 Claims, 8 Drawing Sheets

(51) Int. Cl.
    *G01N 33/50*     (2006.01)
    *G01N 15/01*     (2024.01)

(56) References Cited

U.S. PATENT DOCUMENTS

| | | |
|---|---|---|
| 2005/0002826 A1 | 1/2005 | Oguni et al. |
| 2007/0105231 A1 | 5/2007 | Riley et al. |
| 2017/0074863 A1* | 3/2017 | Masuda ............. G01N 15/1429 |
| 2019/0048365 A1* | 2/2019 | Castora ................ C12N 15/873 |

FOREIGN PATENT DOCUMENTS

| | | |
|---|---|---|
| CN | 101750274 A | 6/2010 |
| CN | 101988082 A | 3/2011 |
| CN | 103323582 A | 9/2013 |
| CN | 104749144 A | 7/2015 |
| CN | 106525666 A | 3/2017 |
| CN | 107525758 A | 12/2017 |
| WO | WO 9604544 A1 | 2/1996 |

\* cited by examiner

A

B

A

B

A

B

A

B

A

B

A

B

A

B

REAGENT, METHOD FOR ANALYZING PLATELETS AND BLOOD CELL ANALYZER

CROSS-REFERENCE

This application is a continuation of International Application No. PCT/CN2019/084648, filed Apr. 26, 2019, which claims priority benefit of Chinese Patent Application No. 201810402750.X, filed Apr. 28, 2018, the contents of which are incorporated herein by reference.

TECHNICAL FIELD

The present disclosure relates to a method for analyzing platelets and, in particular, to a method for analyzing platelets by using a dye.

BACKGROUND ART

Human blood contains various types of cells, such as red blood cells, white blood cells, platelets, etc. Platelets are non-nucleated cells with a diameter of 2-3 microns, and normal human blood contains 150,000 to 350,000 platelets per microliter.

The electrical impedance method is one of the commonly used measurement methods for platelets. This method is as follows: a sample containing blood cells is passed through an aperture with two electrodes; the impedance changes as a blood cell (such as a platelet) passes through, thus an impedance pulse is generated; and then the detected pulses are drawn as a histogram for analysis. In normal blood, the volume of a platelet is the smallest, the volume of a white blood cell is the largest, and the volume of a red blood cell is intermediate. The detected pulse intensity is related to the volume of the cell passing through the aperture, therefore different types of cells can be differentiated by volume division. However, when some special samples (such as samples containing platelets relatively large in volume and red blood cells relatively small in volume) are tested using this method, the detection accuracy and precision of platelets will be affected. These special samples usually come from subjects with diseases, so the deviation of detection values will have adverse effects on clinical diagnosis.

For this situation, a method for labeling and counting platelets by using a labeled antibody specific to surface antigens of platelets has been developed, see, e.g., American Journal of Clinical Pathology (2001): 115, pp. 460-464. This method requires an antigen-antibody reaction during the test, so it takes a long time to obtain results. Therefore, this method is not suitable for measurements that are required for urgent judgments, such as whether blood transfusion is required or not, etc. Moreover, detection reagents used in this method are also relatively expensive.

Currently, flow cytometry has been widely used for quickly measuring cells in blood. For example, U.S. Pat. No. 6,114,173 discloses a method for measuring reticulocytes and red blood cells and counting platelets, in which a sphering reagent is used to treat a blood sample, a cationic dye (Oxazine 750) is also used to quickly stain RNA of reticulocytes, and then a flow cytometer is used to measure scattered light and absorbed light in the sample, thereby differentiating reticulocytes, red blood cells and platelets.

U.S. Pat. No. 4,882,284 discloses a method for identifying white blood cells in whole blood without hemolysis from red blood cells and platelets, in which a fluorescence dye (Oxazine 170) absorbing red light is contacted with whole blood without hemolysis, and then a flow cytometer is used to differentiate white blood cells from red blood cells and reticulocytes and classifying white blood cells.

A reagent and a method for measuring reticulocytes are disclosed in U.S. Pat. No. 5,891,731, wherein the reagent comprises at least one dye (Oxazine 750) for specifically staining reticulocytes and at least another dye for specifically staining white blood cells, and reticulocyte populations can be clearly differentiated from white blood cell populations after treatment.

Although the above-mentioned documents all adopts dyes for staining blood cells to analyze blood sample, on the one hand, they are all performed under a non-hemolysis condition; and on the other hand, they are all unrelated to differentiate platelets by way of staining platelets with a dye.

For this situation, a specific dye is disclosed in SYSMEX Inc.'s Chinese Patent Application Publication CN 101173921, which is capable of effectively differentiating platelets from impurities such as other blood cells, lipid particles and the like in the direction of fluorescence. However, this method needs to be implemented in a separate test channel when differentiating platelets, which makes instruments more complicated, thereby inevitably increasing costs. Besides, like the fore-mentioned documents, this method is also performed under a non-hemolysis condition, and detecting platelets under a hemolysis condition is also not disclosed.

In practice, in a traditional blood analysis system, it is particularly important to classify and count white blood cells, and it is generally required to lyse red blood cells (namely under a hemolysis condition) when detecting white blood cells, thereby producing impurities such as a large number of cell fragments and the like, which makes it more difficult to measure platelets. Therefore, for the present, it is common to measure platelets under a non-hemolysis condition in a separate channel.

Detecting platelets in a more severe environment and under a more difficult hemolysis condition has relatively more clinical significance. If platelets can be detected quickly and accurately under a hemolysis condition, the disadvantage that platelet detection is susceptible to small red blood cells in an impedance channel can be eliminated, and meanwhile classification and counting of white blood cells can be achieved as well, so that it is beneficial to analyze each composition in blood in a single channel.

Therefore, there is a need to detect platelets quickly and conveniently under a hemolysis condition in the field of blood detection.

SUMMARY OF THE DISCLOSURE

In view of the above situations, an object of the present disclosure is to provide a reagent an analysis method capable of detecting platelets under a hemolysis condition.

A further object of the present disclosure is to provide a reagent and an analysis method capable of detecting platelets under a hemolysis condition and simultaneously providing an alarm about reticulocytes.

Another further object of the present disclosure is to provide a reagent and an analysis method for effectively detecting platelets and white blood cells and providing an alarm about reticulocytes simultaneously in a single channel.

Another further object of the present disclosure is to provide a reagent and an analysis method for effectively detecting platelets, white blood cells and/or reticulocytes simultaneously in a single channel.

To achieve the above-mentioned objects, in a first aspect, the present disclosure provides a reagent, wherein the reagent comprises:
a first reagent as a hemolytic agent; and
a second reagent which is a membrane-specific dye or a mitochondrion-specific dye.

In an embodiment, the membrane-specific dye is selected from DiA, DiD, DiI, DiO, DiR, DiS, FDA, Alexa Fluor 488 and Super Fluor 488.

According to another embodiment, the mitochondrion-specific dye is selected from Janus Green B, MitoLite Red, Rhodamine 123 and Mitotracker series.

In one embodiment, the mitochondrion-specific dye is Rhodamine 123, Mitotracker Deep Red or Mitotracker Red.

In the present disclosure, the Mitotracker series of dyes may comprise Mitotracker Green, Mitotracker Deep Red, Mitotracker Red, etc.

In some embodiments, the second reagent of the present disclosure further comprises a variant structure, parent of which is selected from the above-mentioned dyes.

According to another embodiment, the reagent of the present disclosure further comprises a third reagent as a nucleic acid dye.

According to some embodiments, the first reagent may comprise at least one hemolytic agent selected from alkyl glycoside, triterpene saponin, and steroidal saponin.

Preferably, the alkyl glycoside is selected from glycoside compounds having the general formula I:

R—(CH$_2$)$_n$—CH$_3$  (I)

wherein R is selected from a group consisting of monosaccharide, deoxy monosaccharide and polysaccharide, and n is an integer of 5-17.

In some embodiments, the first reagent further comprises:
a nonionic surfactant having the general formula II:

R$_1$-R$_2$—(CH$_2$CH$_2$O)$_m$—H  (II)

wherein R$_1$ is a C8-C23 alkyl group, R$_2$ is —O—,

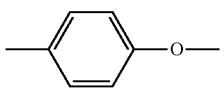

or —COO—, and m is an integer of 10 to 50; and
optionally, at least one organic acid or a salt thereof, wherein the organic acid or the salt thereof is selected from the group consisting of organic acids having at least one carboxyl group or sulfonic acid group and alkali metal salts thereof.

In a second aspect, the present disclosure provides a method for analyzing a blood sample, comprising:
obtaining a blood sample that is treated with a first reagent and a second reagent;
obtaining optical information of the blood sample;
differentiating platelets and/or counting platelets according to the optical information;
wherein the first reagent is a hemolytic agent, and the second reagent is a membrane-specific dye or a mitochondrion-specific dye.

In an embodiment, the membrane-specific dye is selected from DiA, DiD, DiI, DiO, DiR, DiS, FDA, Alexa Fluor 488 and Super Fluor 488.

According to another embodiment, the mitochondrion-specific dye is selected from Janus Green B, MitoLite Red, Rhodamine 123 and Mitotracker series.

In the present disclosure, the Mitotracker series of dyes may comprise Mitotracker Green, Mitotracker Deep Red, Mitotracker Red, etc.

In the present disclosure, the hemolytic agent is capable of lysing red blood cells in the blood sample into fragments having light scattering characteristics significantly different from those of platelets.

In an embodiment, the hemolytic agent may be at least one selected from alkyl glycoside, triterpene saponin, and steroidal saponin.

In an embodiment, the method further comprises differentiating white blood cells according to the optical information.

In another embodiment, the method further comprises classifying white blood cells according to the optical information.

In an embodiment, the method further comprises providing an alarm about reticulocytes according to the optical information.

In another embodiment, in addition to the first reagent and the second reagent, the method of the present disclosure also adopts a third reagent to treat the blood sample, and the third reagent is a nucleic acid dye.

In an embodiment, the method of the present disclosure further comprises differentiating reticulocytes according to the optical information.

In an embodiment, the optical information comprises fluorescence intensity information and scattered light intensity information.

Preferably, the scattered light intensity information is selected from one or two of forward scattered light intensity information and side scattered light intensity information.

In another embodiment, the scattered light intensity information is forward scattered light intensity information.

In a third aspect, the present disclosure provides a method for analyzing a blood sample in a single channel under a hemolysis condition, and the method is characterized in that a membrane-specific dye and a mitochondrion-specific dye is used to contact with the blood sample.

In an embodiment, platelet membranes or mitochondria are stained by the membrane-specific dye or the mitochondrion-specific dye, so that platelets are differentiated from blood ghost.

In a fourth aspect, the present disclosure provides a blood cell analyzer, comprising:
a sampling part comprising a sampler configured to suck a blood sample;
a reaction part comprising a mixing chamber and a reagent supply part, wherein the mixing chamber is in fluid connection with the sampler and the reagent supply part, the mixing chamber is configured to mix the blood sample with a first reagent and a second reagent and to perform hemolysis and stain on the blood sample to prepare a treated blood sample, the reagent supply part is configured to supply a reagent to the mixing chamber, wherein the first reagent is a hemolytic agent and the second reagent is a membrane-specific dye or a mitochondrion-specific dye;
a detection part comprising a light source, a detection area and at least one optical detector, wherein the light source is configured to align light beams to the detection area that is in fluid connection with the mixing chamber, the detection area is configured for particles of the treated blood sample to pass through one by one, the at least one optical detector is configured to acquire a fluorescence signals, forward scattered light intensity signals and optional side scattered light intensity signals of the particles in the detection area; and an analysis part comprising a processor and a non-transitory computer readable storage medium storing a computer program, wherein the processor is operatively connected with the optical detector, and when the computer program is executed by the processor, the processor is caused to generate a scatter diagram of blood cells based on the fluorescence signals and the forward scattered light intensity signals, and to differentiate and count platelets according to the scatter diagram.

In an embodiment, when the computer program is executed by the processor, the processor is further caused to generate a scatter diagram of blood cells based on the fluorescence signals and the forward scattered light intensity signals, and to provide an alarm about reticulocytes based on the scatter diagram.

In some embodiments, when the computer program is executed by the processor, the processor is further caused to generate a scatter diagram of blood cells based on the fluorescence signals and the forward scattered light intensity signals, and to differentiate white blood cells and count white blood cells or classify and count white blood cells based on the scatter diagram.

In a more preferable embodiment, the mixing chamber is configured to mix the blood sample with the first reagent, the reagent and a third reagent, wherein the third reagent is a nucleic acid; and when the computer program is executed by the processor, the processor is caused to generate a scatter diagram of blood cells based on the fluorescence signals and the forward scattered light intensity signals, and to differentiate and count reticulocytes based on the scatter diagram.

Analyzing a blood sample by using the reagent of the present disclosure has the advantages as follows: antibody labeling is not needed for platelets in the process, thus saving time and cost; platelets can be effectively differentiated from fragmented blood cells and impurities, and an accurate analysis result is thus obtained; and platelet analysis is performed under a hemolysis condition, thereby providing a basis for subsequent classification and counting of white blood cells in a single channel.

DETAILED DESCRIPTION OF EMBODIMENTS

Figure 1:
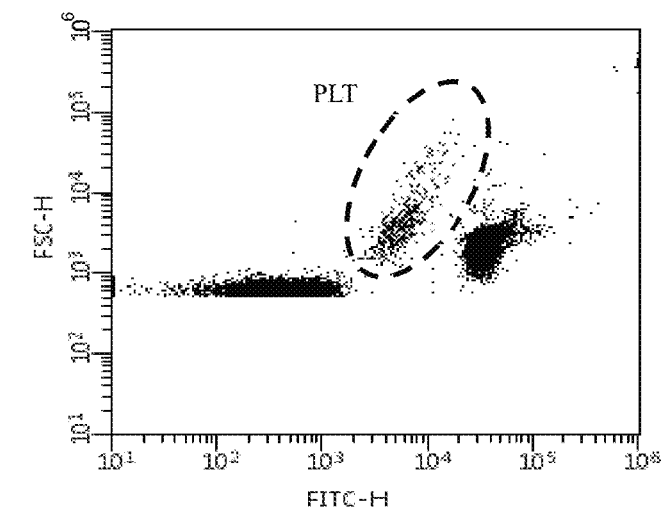
FIG. 1 illustrates the staining and differentiating effects of the dye Alexa Fluor 488 on (A) platelets and (B) white blood cells under a hemolysis condition.
Figure 1:
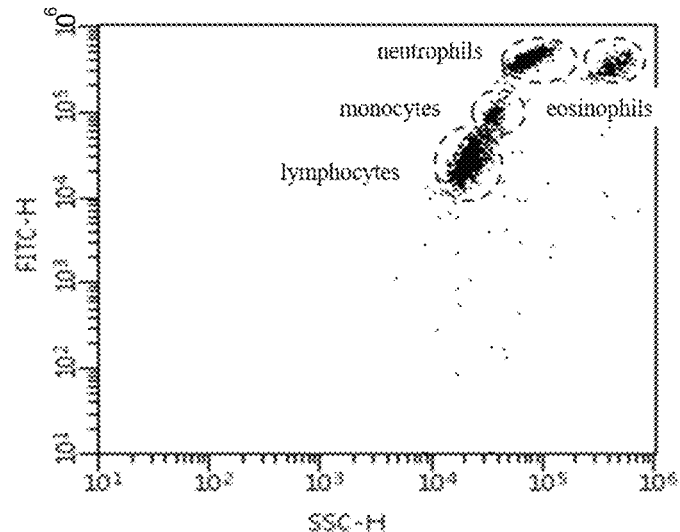

The technical solutions in the embodiments of the present disclosure will be described clearly and fully in combination with the accompanying drawings in the embodiments of the present disclosure. Obviously, the described embodiments are only some embodiments of the present disclosure, but not all embodiments. Based on the embodiments in the present disclosure, all other embodiments obtained by those of ordinary skill in the art without any creative efforts shall fall within the protection scope of the present disclosure.

Throughout the specification, unless otherwise specifically stated, the terms used herein should be understood to have the meaning commonly used in the art. Therefore, unless otherwise defined, all technical and scientific terms used herein have the same meaning as commonly understood by those of ordinary skill in the art to which the present disclosure belongs. If there are conflicts, this specification takes precedence.

As previously mentioned, in conventional methods for detecting platelets, the electrical impedance method is generally adopted, but platelets cannot be detected accurately when the electrical impedance method is used to detect some special blood samples. While detection results obtained by a method using a platelet-specific antibody are relatively accurate, the detection takes a long time and is expensive in price, thus there is a great limitation on its applicable scope.

Therefore, in Chinese Patent CN101173921A, platelets are detected in a separate channel by using an optical detection method combined with a specific dye, which solves the above-mentioned problem to a certain extent but is still unsatisfactory. This is mainly because the method is performed under a non-hemolysis condition, and under the non-hemolysis condition, there is no large number of red blood cell fragments generated due to hemolysis, thereby avoiding interference to platelet detection, which makes the platelet detection easier to implement. But in other words, when a conventional blood cell analysis is performed under the non-hemolysis condition, an additional detection channel will be inevitably used, which not only requires more sample amount, but also makes instruments more complicated.

If platelet analysis can be achieved under a hemolysis condition, it will be beneficial for differentiating between platelets and other blood cells in a single channel. For this purpose, the inventors did researches on commercial dyes in the prior art and accidentally found that platelets can be differentiated under a hemolysis condition by using a platelet membrane-specific dye or a platelet mitochondrion-specific dye, thus the present disclosure is accomplished. By adopting the dyes of the present disclosure to analyze platelets under a hemolysis condition, interference caused by abnormal red blood cells, such as fragile red blood cells, small red blood cells and the like in special samples, and impurities to platelet detection can be avoided.

Further surprisingly, by treating a blood sample by the dyes of the present disclosure under a hemolysis condition, not only platelets can be detected, but also white blood cells can be classified and counted (referring to embodiments described in detail below), thus the analysis of platelets and the classification and counting of white blood cells can be accomplished in a single channel using one kind (type) of dyes, which greatly reduces the detection time and simplifies the operation procedures and complication of instruments.

Furthermore, in one aspect, when the dyes of the present disclosure are adopted to stain platelets, high fluorescence reticulocytes can also be displayed to prompt that reticulocytes are present in the sample, namely, by adopting the dyes of the present disclosure, platelets can be displayed and an alarm for reticulocytes can be achieved simultaneously; and in another aspect, the dyes of the present disclosure can be combined with nucleic acid dyes to achieve platelet analysis, reticulocyte analysis and classification and counting of white blood cells in one hemolysis channel.

Furthermore, for better differentiating platelets from red blood cell fragments under a hemolysis condition and achieving accurate and precision detection of platelets, red blood cells can be lysed relatively deeply while the dyes of the present disclosure are used, so that cell membranes of red blood cells are broken into smaller fragments, thereby a red blood cell fragment region and a platelets region can be clearly differentiated according to a scatter diagram obtained through optical detection.

Reagents

In a first aspect, the present disclosure provides a reagent for analyzing a blood sample, wherein the reagent comprises:
  a first reagent as a hemolytic agent; and
  a second reagent which is a membrane-specific dye or a mitochondrion-specific dye.

As used herein, as the second reagent, the "membrane-specific dye" refers to a fluorescence dye capable of specifically staining cell membranes, so that platelets can be identified from impurities such as cell fragments, etc. Similarly, the "mitochondrion-specific dye" refers to a fluorescence dye capable of specifically staining cell mitochondria, so that platelets can be identified from impurities such as cell fragments, etc.

The membrane-specific dye in the present disclosure may comprise any commercial membrane-specific dyes including but not limited to DiA, DiD, DiI, DiO, DiR, DiS, FDA, Alexa Fluor 488, and/or Super Fluor 488.

In an embodiment, the membrane-specific dye is Alexa Fluor 488 and/or DiD.

The mitochondrion-specific dye in the present disclosure may comprise any commercial mitochondrion dyes including but not limited to Janus Green B, MitoLite Red, Rhodamine 123, and Mitotracker series.

In an embodiment, the mitochondrion-specific dye is Mitotracker Deep Red, Rhodamine 123, or Mitotracker Red.

The Mitotracker series in the present disclosure comprise but are not limited to Mitotracker Green, Mitotracker Deep Red, and Mitotracker Red.

In the reagent of the present disclosure, the first reagent and the second reagent may be provided in a same package, or may be provided respectively in a separate package.

Preferably, the first reagent and the second reagent of the present disclosure are provided respectively in a separate package, wherein the first reagent may be prepared in an aqueous solution form, and the second reagent may be prepared in a non-aqueous solution form.

Similarly, when a third reagent is included, the first reagent, the second reagent and the third reagent may be provided in a same package, or may be provided respectively in a separate package. Preferably, the first reagent, the second reagent and the third reagent of the present disclosure are provided respectively in a separate package, wherein the first reagent may be prepared in an aqueous solution form, and the second reagent and the third reagent may be prepared in a non-aqueous solution form.

As the second reagent, the dye of the present disclosure further comprises variant structures using the above-mentioned membrane-specific dyes or mitochondrion-specific dyes as parents, and these variant structures have similar staining properties with their parents. Exemplary variant structures comprise: DiD perchlorate and DiD trifluoromethanesulfonate using DiD as parent; DiIC12 (3) perchlorate, DiIC12 (3) trifluoromethanesulfonate, DiIC16 (3) perchlorate, DiIC18 (3)-DS, DiIC18 (5)-DS, DiIC1 (5) iodide, 9-DiI mesylate, DiI iodide, DiI perchlorate and DiI trifluoromethanesulfonate using DiI as parent; DiOC2 (3) iodide, DiOC3 (3) iodide, DiOC7 (3) iodide, DiOC16 (3) perchlorate, DiOC5 (3) iodide, DiOC6 (3) iodide, 1,1'-bioctadecanol ester group-5,5'-diphenyl-3,3,3',3'-tetramethylindole carbon chloride hydrochloride and DiO perchlorate using DiO as parent; DiR iodide using DiR as parent; DiSC2 (3) and DiSC3 (5) using DiS as parent. However the present disclosure is not limited thereto, variant structures modified based on the membrane-specific dyes or mitochondrion-specific dyes of the present disclosure as parents all fall within the protection scope of the present disclosure as long as the variant structures have similar properties to their parents and can achieve similar effects to their parents.

In the present disclosure, variant structures of the dyes comprise commercial variant structures or non-commercial variant structures. According to the name, the structure and the like of the dyes, those skilled in the art can obtain variant structures (such as commercial variant structures) or derived structures using known dyes as parents from the prior art; meanwhile, non-commercial variant structures or derived structures can be obtained according to the parent structures and/or existing variant structures, and it can be reasonably expected that these variant structures can achieve a staining effect similar to that of their parents. These variant structures all fall within the protection scope of the present disclosure.

The second reagent of the present disclosure is preferably dissolved in a suitable organic solvent, and those skilled in the art can select a suitable solvent, for example, methanol, ethanol, ethylene glycol, glycerin, etc. The concentration of the second reagent of the present disclosure in the solvent is about 20 mg/L to 40 mg/L, preferably about 30 mg/L.

As used in the present disclosure, as the first agent, "hemolytic agent" refers to an agent used to destroy red blood cell membranes, thereby facilitating the classification of white blood cells.

The hemolytic agent is not particularly limited in the present disclosure, and any hemolytic agent known in the art can be applied to the reagent and method of the present disclosure as long as it can achieve a general hemolysis effect. Exemplary hemolytic agents are M-68LD, M-60LD, M-50LEO (I) and M-50LEO (II) (Mindray Inc.); WDF (Sysmex Inc.), etc. However, the present disclosure is not limited thereto.

As an example, the hemolytic agent of the present disclosure may also be a hemolytic agent with a deep lysis ability, the "hemolytic agent with a deep lysis ability" means that the cell membranes of red blood cells can be broken into smaller fragments in comparison with that of a general hemolysis situation, thereby being more conducive to differentiate platelets from cell membrane fragments. For example, Chinese Patent CN200910109215.6 discloses a glycoside compound, the entire content of the patent document is incorporated into this application by reference.

For instance, glycoside compounds that can be used as a "hemolytic agent with a deep lysis ability" may be alkyl glycosides, triterpene saponins, steroidal saponins, etc., and the cell membranes of red blood cells can be lysed into smaller fragments by increasing usage amount or selecting a suitable glycoside compound.

A specific hemolytic agent may be a glycoside compound having the general formula I:

$$R—(CH_2)_n—CH_3 \quad (I)$$

wherein R is selected from a group consisting of monosaccharide, deoxy monosaccharide and polysaccharide, and n is an integer of 5-17.

The above glycoside compound capable of quickly lysing red blood cells. The glycoside compound is a compound formed by dehydrating the hemiacetal hydroxyl group of saccharide (or polysaccharide) and the hydroxyl group of alkanol. The glycoside compound in the hemolytic agent of the present disclosure may be a single compound or a mixture of two or more glycoside compounds in accordance with the above-mentioned general formula.

In the general formula (I), the monosaccharide is not particularly limited. The commonly used monosaccharide may be selected from pentose, methyl pentose and hexose, but is not limited thereto. The pentose comprises such as arabinose, xylose, ribose, lyxose, etc. The methyl pentose comprises such as fusantose, rhamnose, quinovose, etc. The hexose comprises such as glucose, mannose, fructose, galactose and sorbose. The deoxy monosaccharide is also not particularly limited, and comprises such as deoxyribose, deoxyglucose, etc., but is not limited thereto. The polysaccharide comprises such as maltose, sucrose, etc., but is not limited thereto. n is preferably an integer of 6 to 14, more preferably an integer of 7 to 11.

The glycoside compound having the general formula I may specifically be octyl glucoside, nonyl glucoside, decyl glucoside, dodecyl maltoside, myristyl maltoside and dodecyl glucoside, preferably octyl glycoside, nonyl glucoside, decyl glucoside and dodecyl maltoside, more preferably decyl glucoside and dodecyl maltoside.

The concentration of the glycoside compound having the general formula I in the hemolytic agent of the present disclosure varies according to the properties of the selected glycoside, the reaction time, the reaction temperature and the dosage of other components. Generally, the dosage is within the range from 0.025 g/L to 10 g/L, preferably within the range from 0.1 g/L to 5.0 g/L.

The first reagent in the first embodiment preferably further comprises:
a nonionic surfactant having the general formula II:

$$R_1-R_2—(CH_2CH_2O)_m—H \quad (II)$$

wherein $R_1$ is a C8-C23 alkyl group, $R_2$ is —O—,

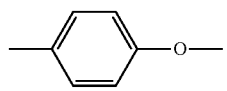

or —COO—, and m is an integer of 10 to 50; and
optionally, at least one organic acid or a salt thereof, wherein the organic acid or the salt thereof is selected from the group consisting of organic acids having at least one carboxyl group or sulfonic acid group and alkali metal salts thereof.

The nonionic surfactant having the general formula II is capable of binding to cell membranes of white blood cells to a certain extent, so as to achieve an effect of protecting the cell membranes of white blood cells and platelets from being influenced by the aforementioned glycoside compounds, thereby maintaining or substantially maintaining their cell morphologies.

According to an embodiment, in the nonionic surfactant having the general formula II, preferably, R1 is a C8-C18 linear alkyl group. The C8-C18 linear alkyl group may specifically be octyl, decyl, lauryl, tetradecyl, hexadecyl or stearyl. More preferably, R1 is a C12-C16 linear alkyl group, which may specifically be lauryl, tetradecyl, or hexadecyl. R2 preferably is —O—. m is from 10 to 50, preferably from 15 to 30.

Specific examples of the nonionic surfactant having the general formula II may be cetanol polyoxyethylene (15) ether, dodecanol polyoxyethylene (21) ether, cetanol polyoxyethylene (23) ether, cetanol polyoxyethylene (25) ether and cetanol polyoxyethylene (30) ether, but are not limited thereto.

The concentration of the nonionic surfactant having the general formula II is not particularly limited, but may be 0.03 g/L to 1.5 g/L, preferably 0.05 g/L to 1.0 g/L.

In the present disclosure, the nonionic surfactant may be used as a single substance or a mixture of two or more substances. Depending on the type of the nonionic surfactant used, the concentration thereof in the hemolytic agent varies. In general, the concentration of the nonionic surfactant with a longer alkyl chain and more repeat units in the polyoxyethylene part is relatively low.

In the present disclosure, the compounds having the general formula I and the general formula II are used cooperatively, so that on the one hand, the effect of quickly and deeply lysing red blood cells can be achieved and on the other hand, cell membranes of platelets can be protected in order to effectively detect the platelets.

According to the selected compounds having the general formula I and the general formula II, their dosage ratio also varies. However, in general, the dosage ratio of the compounds having the general formula I and the general formula II is 1:100 to 1:3, preferably 1:25 to 1:5, and more preferably 1:10 to 1:5.

According to an embodiment of the present disclosure, the first reagent further comprises at least one organic acid or a salt thereof to improve the differentiation degree of scattered light of white blood cells. The organic acid is preferably selected from the group consisting of C1-6 alkyl mono-, di-, or tri-carboxylic acid which is unsubstituted or substituted with a hydroxy group or an amino group, C1-6 alkyl sulfonic acid which is unsubstituted or substituted with a hydroxy group or an amino group, C6-10 aryl C1-6 alkyl acid, C6-10 aryl bi(C1-6 alkyl acid) and C6-10 aryl sulfonic acid.

Specific examples of the organic acid and its salt may be formic acid, acetic acid, benzoic acid, citric acid (3-hydroxy-1,3,5-pentyl triacid), malic acid (2-hydroxysuccinic acid), benzenedicarboxylic acid, benzenesulfonic acid, α-naphthalenesulfonic acid, taurine, etc. and their alkali metal salts such as sodium salts and potassium salts, but are not limited thereto.

The concentration of the organic acid or organic acid salt in the hemolytic agent is 0.05 g/L to 2 g/L, preferably 0.1 g/L to 0.5 g/L.

As used in the present disclosure, as the third reagent, the "nucleic acid dye" refers to a dye capable of staining nucleic acids of reticulocytes, so that the reticulocytes can be differentiated from blood cells or impurities.

The nucleic acid-specific dye used in the present disclosure is not particularly limited. Commercialized nucleic acid fluorescence dyes and nucleic acid-specific fluorescence dyes already disclosed in some patent applications may all be applied to the present disclosure. Examples of the commercialized nucleic acid fluorescence dyes are Thermofisher's SYTO series nucleic acid dyes. In addition, fluorescence dyes disclosed in Chinese Patent Application CN201010022414.6, anthocyanin dyes disclosed in CN200910109215.6, fluorescence dyes disclosed in CN200810216864.1, etc., may all be applied to the present disclosure. The entire contents of the above patent documents are incorporated herein by reference.

The third reagent of the present disclosure is preferably dissolved in an organic solvent with a concentration ranging from 0.002 ppm to 2000 ppm, and a preferable concentration ranging from 0.03 ppm to 20 ppm.

Method

In one aspect, the present disclosure provides a method for analyzing a blood sample, comprising:
treating the blood sample with a first reagent and a second reagent;
obtaining optical information of the treated blood sample; and analyzing platelets according to the optical information;
wherein the first reagent is a hemolytic agent, and the second reagent is a membrane-specific dye or a mitochondrion-specific dye.

In an embodiment, the method further comprises differentiating white blood cells according to the optical information.

In another embodiment, the method further comprises classifying white blood cells according to the optical information.

In an embodiment, the method further comprises providing an alarm about reticulocytes according to the optical information.

In another embodiment, in addition to the first reagent and the second reagent, the method of the present disclosure also adopts a third reagent to treat the blood sample, and the third reagent is a nucleic acid dye.

In an embodiment, the method of the present disclosure further comprises differentiating reticulocytes according to the optical information.

In an embodiment, the optical information comprises fluorescence intensity information and scattered light intensity information.

Preferably, the scattered light intensity information is selected from one or two of forward scattered light intensity information and side scattered light intensity information.

In another embodiment, the scattered light intensity information is forward scattered light intensity information.

In a specific embodiment, platelets can be differentiated by using the fluorescence intensity information and the forward scattered light intensity information.

In another specific embodiment, platelets can be differentiated by using the fluorescence intensity information, the forward scattered light intensity information and the side scattered light intensity information.

In a specific embodiment, white blood cells can be classified and counted by using the fluorescence intensity information and the side scattered light intensity information.

In another aspect, the present disclosure further provides a method for analyzing a blood sample under a hemolysis condition, and the method is characterized in that a membrane-specific dye and a mitochondrion-specific dye is used to contact with the blood sample.

In one embodiment, it is characterized in that platelets in the blood sample are stained by the membrane-specific dye or the mitochondrion-specific dye.

In another aspect, the present disclosure further provides an analysis method, comprising:
1) adding a blood sample to a first reagent of the present disclosure to lyse red blood cells in the blood sample;
2) adding a second reagent of the present disclosure to stain platelets; and
3) determining the number of the platelets;
wherein the step 1) and the step 2) are performed simultaneously or sequentially.

In an embodiment, the analysis method of the present disclosure further comprises: 2') adding a third reagent of the present disclosure to identify reticulocytes, wherein the step 2') can be performed in synchronization with the step 2), performed in synchronization with the step 1), and performed during the steps 1) and 2) or after the steps 1) and 2).

The analysis method of the present disclosure may further comprise: 4) determining the number of the reticulocytes, wherein step 4) and the step 3) may be performed in any sequence.

In an embodiment, the analysis method of the present disclosure further comprises: 5) classifying and counting white blood cells, wherein the step 5) and the steps 3) and 4) may be performed in any sequence.

In an embodiment, the method of the present disclosure is an analysis method for platelets, which can differentiate platelets from cell fragments and impurities, etc., and preferably, the method can achieve alarming about reticulocytes.

In another embodiment, the method of the present disclosure is an analysis method for platelets and white blood cells, which can differentiate platelets and classify and count white blood cells, and the method can be performed in a single channel, and preferably, the method can achieve alarming about reticulocytes.

In another embodiment, the method of the present disclosure is an analysis method for platelets, reticulocytes and white blood cells, which can differentiate platelets, differentiate reticulocytes, and classify and count white blood cells, and the method can be performed in a single channel.

In the method of the present disclosure, the blood sample refers to a blood sample collected from animals, preferably a whole blood sample. The animals are preferably mammals, more preferably primates, and most preferably humans.

In the method of the present disclosure, the first reagent and the second reagent can be simultaneously or sequentially used to treat the blood sample. Besides, when a third reagent is present, treatment can be performed according to the following sequences: the first reagent, the second reagent and third reagent are used in sequence; the first reagent, the third reagent and the second reagent are used in sequence; the first reagent and the second reagent are first used simultaneously, and then the third agent is used; the first reagent and the third reagent are first used simultaneously, and then the second reagent is used; the first reagent is first used, and then the second reagent and the third reagent are used simultaneously; and the first reagent, the second reagent and the third reagent are used simultaneously.

In the method of the present disclosure, the step of using the first reagent for treatment or lysing red blood cells can be achieved through incubation, and the step of using the second reagent and/or the third reagent for treatment or staining can also be achieved through incubation. The incubation conditions (such as mixing ratio, incubation temperature, and incubation time) are not particularly limited in the present disclosure, and those skilled in the art can obtain the incubation conditions by adjustment according to the types of the used reagents based on the conventional parameters, as long as red blood cells in the blood sample can be lysed, and platelets or reticulocytes can be stained. For instance, when the first reagent is used, the ratio of the blood sample and the first reagent may be 1:40 to 1:60, and the blood sample and the first reagent may react at a temperature such as 40° C. to 60° C. for 15~100 seconds, preferably for 40~80 seconds; when the second reagent is used, the ratio of the blood sample and the second reagent may be 1:40 to 1:60, and the blood sample and the second reagent may react at a temperature such as 25° C. to 60° C. for 15~100 seconds, preferably for 40~80 seconds; when the third reagent is used, the ratio of the blood sample and the third reagent may be 1:0.1 to 1:50, preferably 1:1 to 1:5, and the blood sample and the third reagent may react at a temperature such as 20° C. to 50° C. for 15~100 seconds, preferably for 40~80 seconds.

In the analysis method of the present disclosure, after the first, second and/or third reagents are added to the blood sample, mixing operation is optionally performed to shorten the reaction time. The mixing operation may be performed in any way for uniformly mixing the reagents with the blood sample, for example, oscillation, stirring, etc.

In the analysis method of the present disclosure, the treated blood sample is subjected to optical detection, and the optical detection comprises acquiring fluorescence intensity and scattered light intensity, wherein the scattered light intensity comprises forward scattered light intensity (light reception angle is close to 0 degree) and/or side scattered light intensity (light reception angle is close to 90 degrees). Preferably, a flow cytometer is used to analyze the treated sample.

In the method of the present disclosure, counting of platelets is achieved; and when the third reagent is used, the method of the present disclosure achieves counting of reticulocytes.

In the method of the present disclosure, "white blood cell classification" refers to three-, four-, five-classification and the like of white blood cells.

As detailed in the following specific examples, the analysis method using the reagent of the present disclosure is capable of staining platelets under a hemolysis condition and clearly differentiating a red blood cell fragment region and a platelet region by a scatter diagram obtained through optical detection under a hemolytic condition that is more difficult for measurement, thereby achieving quick and accurate detection of platelets under the hemolytic condition.

Further, the analysis method of the present disclosure can not only differentiate platelets from impurities such as cell fragments under a hemolysis condition, but can also stain white blood cells well, so as to count and classify white blood cells, thereby achieving differentiation of platelets and classification and counting of white blood cells in one channel.

Furthermore, in the presence of the third reagent, the analysis method of the present disclosure is further capable of identifying reticulocytes, thereby achieving differentiation of platelets, differentiation of reticulocytes, and classification and counting of white blood cells in one channel.

Instrument

Figure 10:
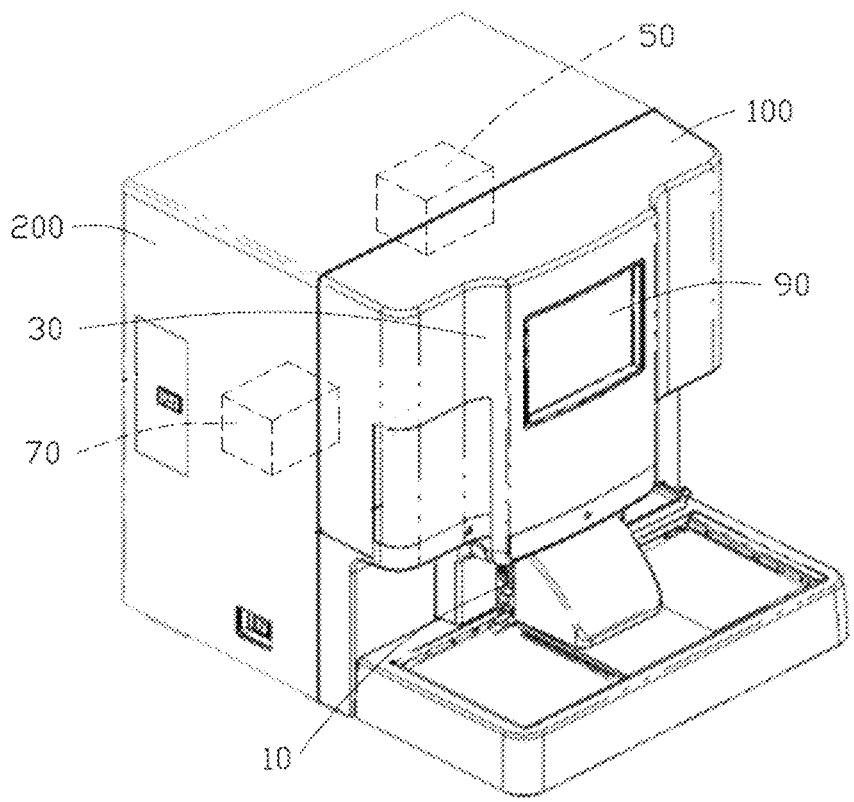
FIG. 10 illustrates a schematic structure diagram of a blood cell analyzer provided by an embodiment of the present disclosure.

The present disclosure further provides a blood cell analyzer, and it will be exemplarily described below in combination with FIG. 10. The blood cell analyzer comprises a first housing 100, a second housing 200, a sampling part 10, a reaction part 30, a detection part 50, an analysis part 70 and an output part 90. In practical applications, the output part 90 may be a user interface. In this embodiment, the detection part 50 and the analysis part 70 are disposed inside the second housing 200 and are disposed on both sides of the second housing 200 respectively. The reaction part 30 is disposed inside the first housing 100, and the output part 90 and the sampling part 10 are disposed on an outer surface of the first housing 100.

The sampling part comprises a sampler for sucking a blood sample;

the reaction part comprises a mixing chamber and a reagent supply par, wherein the mixing chamber is in fluid connection with the sampler and the reagent supply part, the mixing chamber is configured to mix the blood sample with a first reagent and a second reagent of the present disclosure and perform hemolysis and staining on the blood sample to prepare a treated blood sample, and the reagent supply part is configured to supply the reagents to the mixing chamber;

the detection part comprises a light source, a detection area and at least one optical detector, wherein the light source is configured to align light beams to the detection area that is in fluid communication with the mixing chamber, the detection area is configured for particles of the treated blood sample to pass through one by one, and said at least one optical detector is configured to acquire fluorescence signals, forward scattered light intensity signals and side scattered light intensity signals of the particles in the detection area;

the analysis part comprises a processor and a non-transitory computer-readable storage medium storing a computer program, wherein the processor is operatively connected with the optical detector, and when the computer program is executed by the processor, the processor is caused to generate a scatter diagram of blood cells based on the fluorescence signals and the forward scattered light intensity signals, and to differentiate and count platelets according to the scatter diagram; and the output part is operatively connected with the analysis part and is configured to display the result obtained by the analysis part to a user.

In some embodiments, when the computer program is executed by the processor, the processor is further caused to generate a scatter diagram of blood cells based on the fluorescence signals and the forward scattered light intensity signals and to provide an alarm about reticulocytes based on the scatter diagram.

In some preferable embodiments, when the computer program is executed by the processor, the processor is further caused to generate a scatter diagram of blood cells based on the fluorescence signals and the side scattered light intensity signals, and to differentiate white blood cells and count white blood cells or classify white blood cells, and classify and count white blood cells based on the scatter diagram.

In an embodiment, the mixing chamber is configured to mix the blood sample with the first reagent, the second reagent and a third reagent of the present disclosure; and when the computer program is executed by the processor, the processor is further caused to generate a scatter diagram of blood cells based on the fluorescence signals and the forward scattered light intensity signals and to differentiate and count reticulocytes based on the scatter diagram.

The present disclosure will be described in detail below by examples but is not limited thereto.

Example 1

Analysis of Blood Sample by Using Fluorescence Dye Alexa Fluor 488

Reagent Preparation

First Reagent

| | |
|---|---|
| Dodecyl Trimethyl Ammonium Chloride | 550 mg |
| Brij35 | 1.5 g |
| Trishydroxymethyl aminomethane | 13 g |
| Pure Water | 1 L |
| pH | 7.0 |

Second Reagent

| | |
|---|---|
| Dye Alexa Fluor 488 | 30 mg |
| Glycol | 950 ml |
| Methanol | 50 ml |

20 µl of a fresh blood was added to 1 mL of the above-mentioned first reagent solution, and 20 µl of the second reagent was added. After incubation was performed at 35° C. for 60 seconds, a flow cytometer (Mindray BriCyte E6) was used to collect data (the excitation wavelength was 488 nm), the gain was set as 500, 90-degree side fluorescence signals were collected as fluorescence staining information, and forward scattered light intensity information with a measurement angle of 0 degree was also adopted. A cell scatter diagram is shown in FIG. 1.

As seen from FIG. 1A, when the membrane dye Alexa Fluor 488 is used, platelets (in the circle) can be effectively differentiated from blood ghost, and white blood cells can also be stained well by the dye and thus can be classified and counted. The platelet count of the sample was calculated to be 216×109/L through the injection volume and the test particle number of platelets, and the measurement value obtained by adopting a counting method using classic manual microscopic examination was also 216×109/L.

According to FIG. 1B, white blood cells were counted by using the same method, and the obtained result was 8.86× 109/L, while the numerical value measured by a Beckman particle counter Z2 is 8.81×109/L, and the two results have a relatively good consistency therebetween. The ratios obtained by dividing lymphocytes, monocytes, neutrophils and eosinophils were 17.8%, 4.8%, 75.8% and 1.6%, respectively; while after this sample was tested in a Mindray blood cell analyzer 6800, the ratios of lymphocytes, monocytes, neutrophils plus basophils, and eosinophils were 18.1%, 5.1%, 74.8% and 2.0%, respectively. The above-mentioned results show that the white blood cell division performed by the method has a relatively good correlation with the ratios obtained by the blood cell analyzer.

Example 2

Analysis of Blood Sample by Using Dye DiD

Reagent Preparation

First Reagent

| | |
|---|---|
| Tetradecyl Trimethyl Ammonium Chloride | 550 mg |
| Brij35 | 1.5 g |
| Trishydroxymethyl aminomethane | 13 g |
| Pure Water | 1 L |
| pH | 7.0 |

Second Reagent

| | |
|---|---|
| Dye DiD | 30 mg |
| Glycol | 950 ml |
| Methanol | 50 ml |

Figure 2:
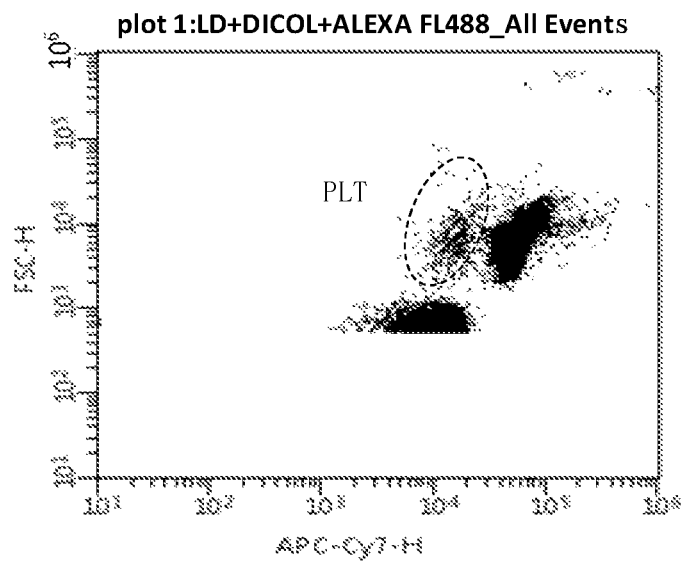
FIG. 2 illustrates the staining and differentiating effects of the dye DiD on (A) platelets and (B) white blood cells under a hemolysis condition.
Figure 2:
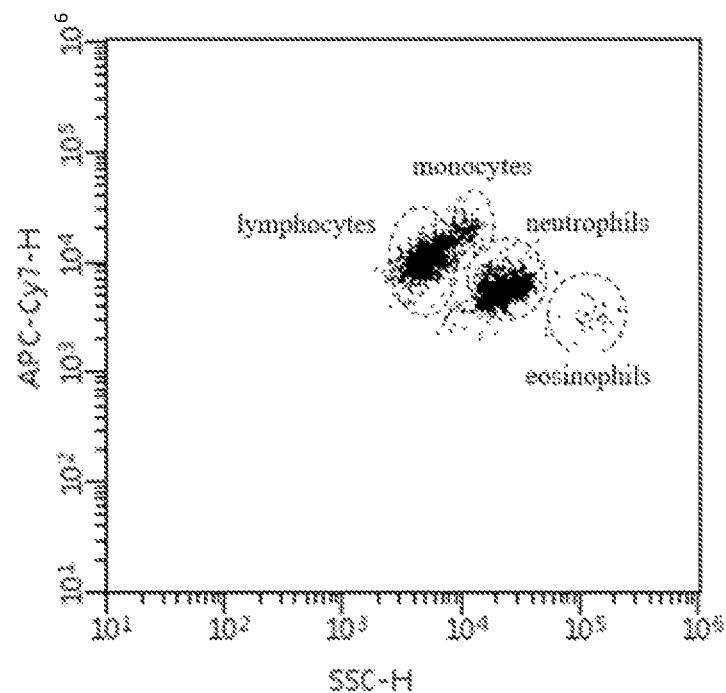

20 µl of a fresh blood was added to 1 mL of the above-mentioned first reagent solution, and 20 µl of the second reagent was added. After incubation was performed at 35° C. for 60 seconds, a flow cytometry (Mindray BriCyte E6) was used to collect data (the excitation wavelength was 633 nm), the gain was set as 500, 90-degree side fluorescence signals were collected as fluorescence staining information, and forward scattered light intensity information with a measurement angle of 0 degree was also adopted. A cell scatter diagram is shown in FIG. 2.

As seen from FIG. 2A, after being stained by the dye, platelets can be effectively differentiated from blood ghost. By dividing the scatter dots of platelets, the concentration of platelets was calculated to be 158×109/L; while the measurement value obtained by adopting a counting method of classic manual microscopic examination was 160×109/L. Therefore, platelet particles can be effectively differentiated and counted by using the dye under a hemolysis condition.

According to FIG. 2B, white blood cells were counted by using the same method, and the obtained result was 4.35× 109/L, while the measurement value obtained by adopting a reference method in combination with the Beckman particle counter Z2 was 4.28×109/L. The two results have a relatively good consistency therebetween. The ratios obtained by dividing lymphocytes, monocytes, neutrophils and eosinophils were 14.8%, 6.8%, 74.5% and 3.9%, respectively; while after this sample was tested in the Mindray blood cell analyzer 6800, the ratios of lymphocytes, monocytes, neutrophils and eosinophils were 15.9%, 7.2%, 72.2% and 4.7%, respectively. The above-mentioned results show that the white blood cell division performed by the above-mentioned method has a relatively good correlation with the ratios obtained by the blood cell analyzer.

Example 3

Analysis of Blood Sample by Using Dye Rhodamine 123

Reagent Preparation

First Reagent

| | |
|---|---|
| Dodecyl Trimethyl Ammonium Chloride | 550 mg |
| Brij35 | 1.5 g |
| Trishydroxymethyl aminomethane | 13 g |
| Pure Water | 1 L |
| pH | 7.0 |

Second Reagent

| | |
|---|---|
| Dye Rhodamine 123 | 30 mg |
| Glycol | 950 ml |
| Methanol | 50 ml |

Figure 3:
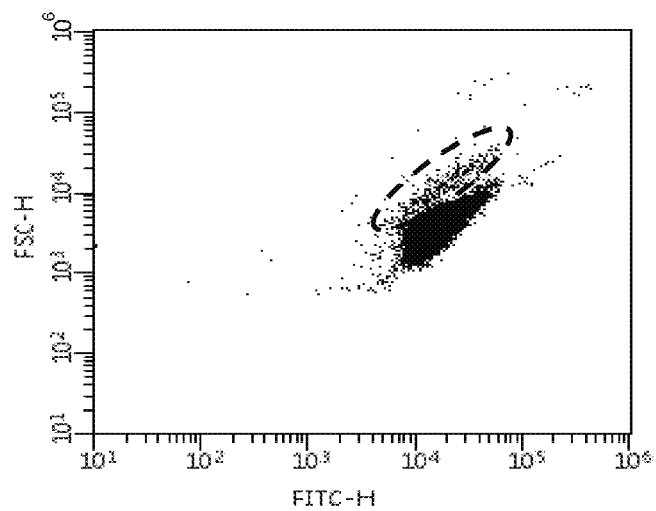
FIG. 3 illustrates the staining and differentiating effects of the dye Rhodamine 123 on (A) platelets and (B) white blood cells under a hemolysis condition.
Figure 3:
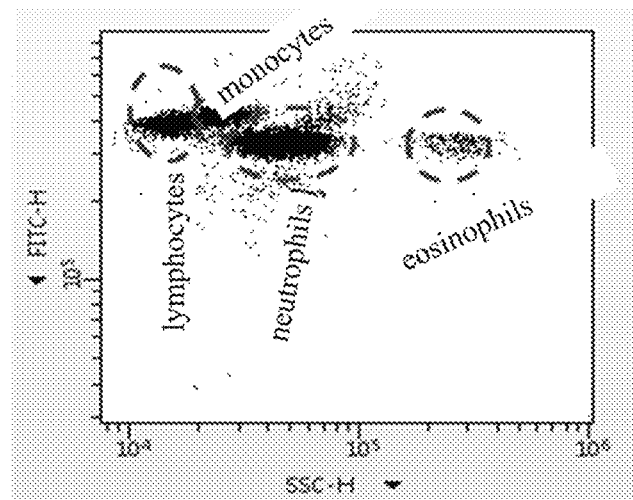

20 μl of a fresh blood was added to 1 mL of the above-mentioned first reagent solution, and 20 μl of the second reagent was added. After incubation was performed at 35° C. for 60 seconds, a flow cytometry (Mindray BriCyte E6) was used to collect data (the excitation wavelength was 488 nm), the gain was set as 500, 90-degree side fluorescence signals were collected as fluorescence staining information, and forward scattered light intensity information with a measurement angle of 0 degree was also adopted. A cell scatter diagram is shown in FIG. 3.

As seen from FIG. 3A, after being stained by the dye Rhodamine 123, platelets can be effectively differentiated from blood ghost. By dividing the scatter dots of platelets, the concentration of platelets was calculated to be 208×109/L; while the measurement value obtained by using a counting method of manual microscopic examination was 201×109/L. Therefore, platelet particles can be effectively differentiated and counted by using the dye Rhodamine 123 under a hemolysis condition.

According to FIG. 3B, white blood cells were counted by using the same method, and the obtained result was 4.02×109/L, while the numerical value measured by adopting a reference method in combination with the Beckman particle counter Z2 was 3.98×109/L. The two results have a relatively good consistency therebetween. The ratios obtained by dividing lymphocytes, monocytes, neutrophils and eosinophils were 15.9%, 7.1%, 71.5% and 5.5%, respectively; while after this sample was tested in the Mindray blood cell analyzer 6800, the ratios of lymphocytes, monocytes, neutrophils and eosinophils were 15.9%, 6.8%, 72.2% and 5.1%, respectively. The above-mentioned results show that the white blood cell division performed by the above-mentioned method has a relatively good correlation with the ratios obtained by the blood cell analyzer.

Example 4

Analysis of Blood Sample by Using Dye Mitotracker Deep Red

Reagent Preparation

First Reagent

| | |
|---|---|
| Tetradecyl Trimethyl Ammonium Chloride | 550 mg |
| Triton 100 | 0.75 g |
| Trishydroxymethyl aminomethane | 13 g |
| Pure Water | 1 L |
| pH | 7.0 |

Second Reagent

| | |
|---|---|
| Dye Mitotracker Deep Red | 30 mg |
| Glycol | 950 ml |
| Methanol | 50 ml |

Figure 4:
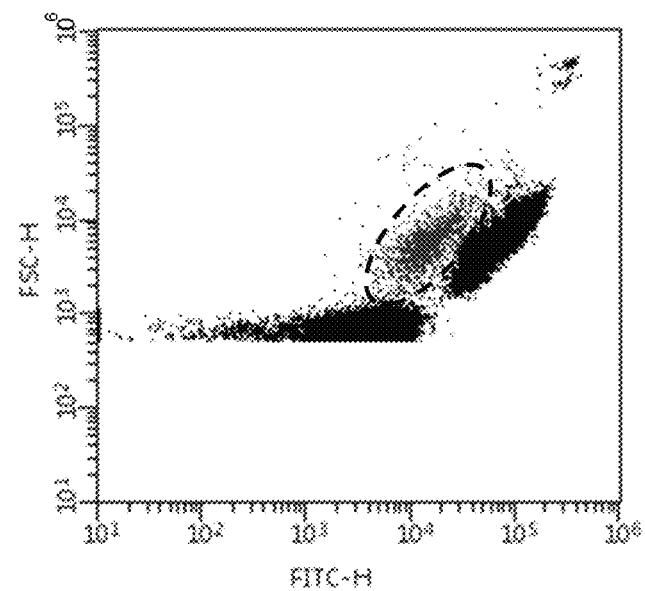
FIG. 4 illustrates the staining and differentiating effects of the dye Mitotracker Deep Red on (A) platelets and (B) white blood cells under a hemolysis condition.
Figure 4:
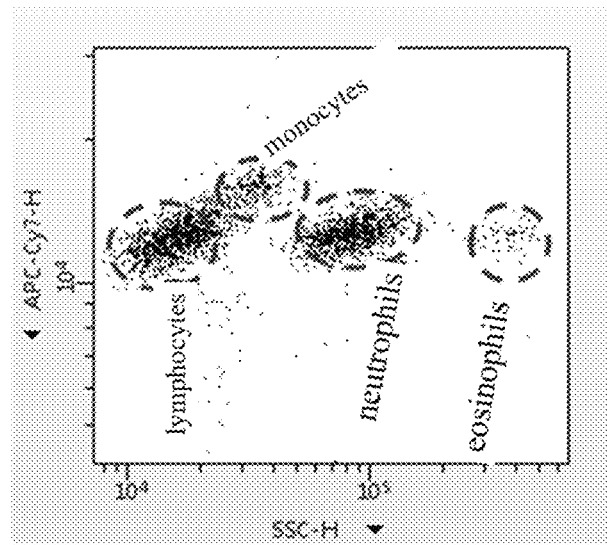

20 μl of a fresh blood was added to 1 mL of the above-mentioned first reagent solution, and 20 μl of the second reagent was added. After incubation was performed at 35° C. for 60 seconds, a flow cytometer (Mindray BriCyte E6) was used to collect data (the excitation wavelength was 633 nm), the gain was set as 500, 90-degree lateral fluorescence signals were collected as fluorescence staining information, and forward scattered light intensity information with a measurement angle of 0 degree was also adopted. A cell scatter diagram is shown in FIG. 4.

As seen from FIG. 4A, when Mitotracker Deep Red was used, platelets can be differentiated from the blood ghost, wherein light-color scatter dots represent platelets, and by dividing the scatter dots of the platelets, the concentration of PLT was calculated to be 165×109/L; while the concentration of PLT obtained by using a counting method of classic manual microscopic examination was 201×109/L. It can be seen that platelets can also be differentiated by using the Dye Mitotracker Deep Red.

According to FIG. 4B, white blood cells were counted by using the same method, and the obtained result was 5.12×109/L, while the measurement value obtained by adopting a reference method in combination with the Beckman particle counter Z2 was 5.08×109/L. The two results have a relatively good consistency therebetween. The ratios obtained by dividing lymphocytes, monocytes, neutrophils and eosinophils were 14.8%, 7.8%, 74.5% and 2.9%, respectively; while after this sample was tested in the Mindray blood cell analyzer 6800, the ratios of lymphocytes, monocytes, neutrophils and eosinophils were 15.9%, 7.2%, 73.2% and 3.7%, respectively. The above-mentioned results show that the white blood cell division performed by the above-mentioned method has a relatively good correlation with the ratios obtained by the blood cell analyzer.

Example 5

Analysis of Blood Sample by Using Dye Mitotracker Red

Reagent Preparation

First Reagent

| | |
|---|---|
| Dodecyl Trimethyl Ammonium Chloride | 550 mg |
| Tween 20 | 1.0 g |
| Trishydroxymethyl aminomethane | 13 g |
| Pure Water | 1 L |
| pH | 7.0 |

Second Reagent

| | |
|---|---|
| Dye Mitotracker Red | 30 mg |
| Glycol | 950 ml |
| Methanol | 50 ml |

Figure 5:
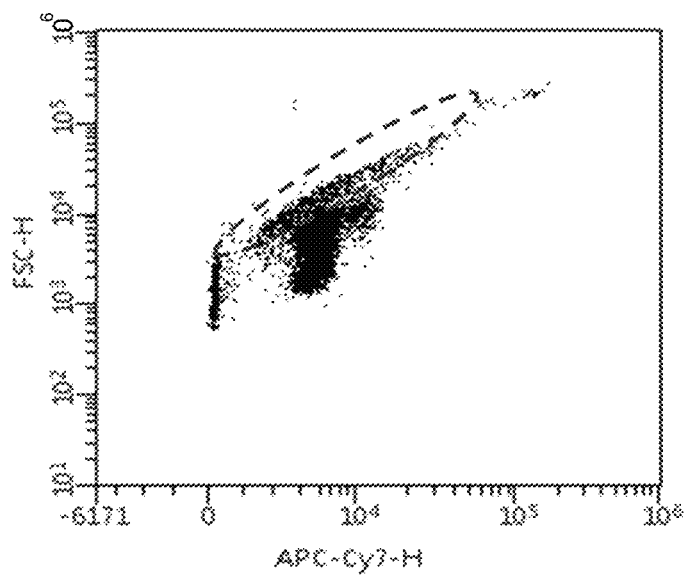
FIG. 5 illustrates the staining and differentiating effects of the dye Mitotracker Red on (A) platelets and (B) white blood cells under a hemolysis condition.
Figure 5:
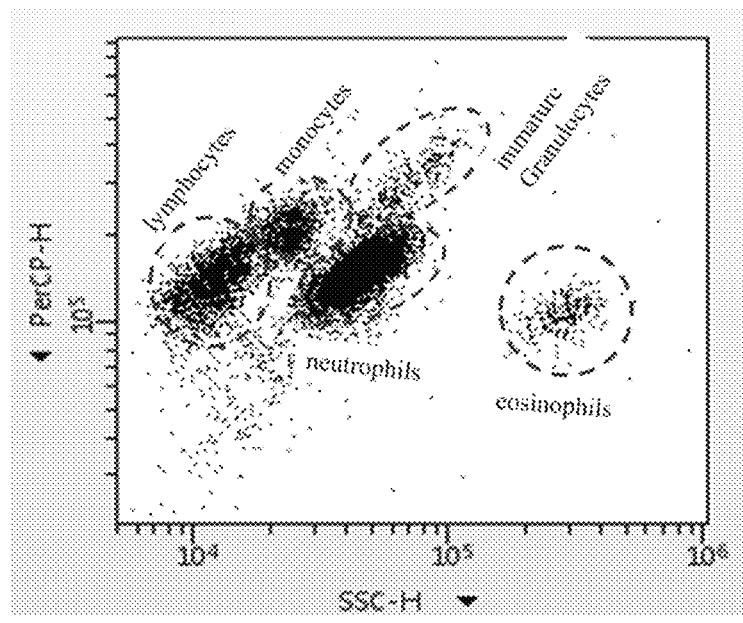

20 μl of a fresh blood was added to 1 mL of the above-mentioned first reagent solution, and 20 μl of the second reagent was added. After incubation was performed at 35° C. for 60 seconds, a flow cytometer (Mindray BriCyte E6) was used to collect data (the excitation wavelength was 488 nm), the gain was set as 500, 90-degree side fluorescence signals were collected as fluorescence staining information, and forward scattered light intensity information with a measurement angle of 0 degree was also adopted. A cell scatter diagram is shown in FIG. 5.

As seen from FIG. 5A, when the dye Mitotracker Red was used, platelets can be effectively differentiated from blood ghost, and meanwhile white blood cells can also be effectively classified based on the staining performance of the dye on white blood cells, thereby achieving effective classification and counting of platelets while detecting white blood cells. Through the injection volume and the test particle number of platelets, the platelet count of the sample was calculated to be 176×109/L, while the measurement value obtained by using a counting method of classic manual microscopic examination was 172×109/L. The two results have a relatively good consistency therebetween.

According to FIG. 5B, white blood cells were counted by using the same method, and the obtained result was 7.65× 109/L, while the measurement value obtained by adopting a reference method in combination with the Beckman particle counter Z2 was 7.73×109/L. The two results have a relatively good consistency therebetween. The ratios obtained by dividing lymphocytes, monocytes, neutrophils, eosinophils, and immature granulocytes were 13.7%, 6.1%, 77.5%, 0.7% and 2.0%, respectively; while after this sample was tested in the Mindray blood cell analyzer 6800, the ratios of lymphocytes, monocytes, neutrophils, eosinophils, and immature granulocytes were 14.1%, 5.8%, 76.2%, 1.9% and 2.0%, respectively. The above-mentioned results show that the white blood cell division performed by the method has a relatively good correlation with the ratios obtained by the blood cell analyzer.

Example 6

Analysis of Blood Sample by Using a Deep Hemolytic Agent and a Membrane Dye

Reagent Preparation

| | |
|---|---|
| Fluorescence Dye Alexa Fluor 488 | 0.8 ppm |
| Alkyl Glycoside (APG0814) ) | 0.6 g/L |
| TRIS | 40 Mm |
| Sodium Citrate | 5 g/L |
| Polyoxyethylene (23) Cetyl Ether | 0.5 g/L |
| pH | 7.5 |

Figure 6:
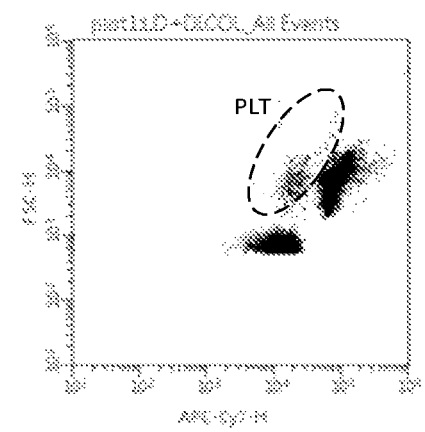
FIG. 6 illustrates a fluorescence-forward scattered light intensity scatter diagram (A) obtained by detecting platelets and reticulocytes by adding a membrane dye under a deep hemolysis condition, and a fluorescence-side scattered light intensity scatter diagram (B) of white blood cells.
Figure 6:
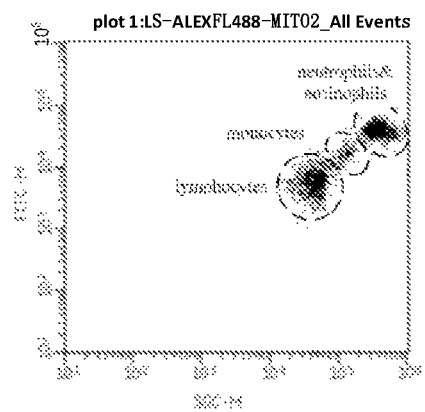

20 μl of a fresh blood sample was added to 1 mL of the solution prepared according to the above-mentioned formula, incubation was performed at 45° C. for 60 seconds, and then a flow cytometer (Mindray BriCyte E6) was used for detection. The excitation wavelength was set as 488 nm, the gain was set as 500, 90° side fluorescence intensity information and 0° forward scattered light intensity information were collected to obtain a two-dimensional cell scatter diagram, as shown in FIG. 6.

As seen from FIG. 6A, the two dark particle clusters (at the lower part and the right side) both consist of lysed red blood cell fragments, and the middle particle cluster consists of platelets, which indicates that the platelets can also be clearly differentiated from the red blood cell fragments by this method.

The same treatment was performed on another 20 μl of the same blood sample, and measurement was performed in the same flow cytometer. The excitation wavelength was set as 633 nm, the gain was set as 100,000 and 90° side fluorescence intensity information and 90° side scattered light intensity information were collected to obtain a cell scatter diagram.

As shown in FIG. 6B, the ratios obtained by dividing lymphocytes, monocytes, and neutrophils plus eosinophils were 16.4%, 6.1%, and 77.5%, respectively; while after this sample was tested on the Mindray blood cell analyzer 6800, the ratios of lymphocytes, monocytes, neutrophils and eosinophils were 16%, 5.8%, 78.2% and 1.9%, respectively. The above-mentioned results show that the white blood cell division performed by the above-mentioned method has a relatively good correlation with the ratios obtained by the blood cell analyzer.

Example 7

Analysis of Blood Sample by Using a Deep Hemolytic Agent and a Mitochondrion Dye Reagent Preparation

| | |
|---|---|
| Fluorescence Dye Mitotracker Red | 0.8 ppm |
| Alkyl Glycoside (APG0814) | 0.6 g/L |
| TRIS | 40 Mm |
| Sodium Citrate | 5 g/L |
| Polyoxyethylene (23) Cetyl Ether | 0.5 g/L |
| pH | 7.5 |

20 μl of a fresh blood sample was added to 1 mL of the solution prepared according to the above-mentioned formula, incubation was performed at 45° C. for 60 seconds, and then a flow cytometer (Mindray BriCyte E6) was used for detection. The excitation wavelength was set as 633 nm, the gain was set as 500, and 90° side fluorescence intensity information and 90° side scattered light intensity information were collected to obtain a two-dimensional cell scatter diagram, as shown in FIG. 7.

Figure 7:
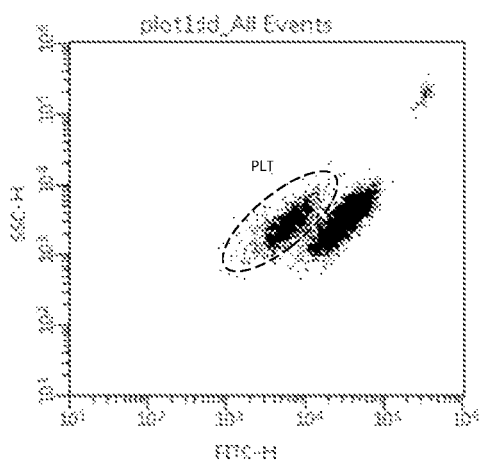
FIG. 7 illustrates a fluorescence-forward scattered light intensity scatter diagram obtained by detecting platelets and reticulocytes by adding a mitochondrion dye under a deep hemolysis condition.

Two particle clusters can be seen in FIG. 7, wherein the particle cluster at the right side consists of lysed red blood cell fragments, and the particle cluster at the left side consists of platelets, which indicates that the platelets can also be clearly differentiated from the red blood cell fragments by this method.

Example 8

Analysis of Blood Sample by Using a Deep Hemolytic Agent, a Membrane Dye and a Nucleic Acid Dye A detection reagent of the present prevention was prepared according to the following formula:

| | |
|---|---|
| Membrane Fluorescence Dye Alexa Fluor 488 | 0.8 ppm |
| Nucleic Acid Dye SYTO9 | 0.6 ppm |
| Alkyl Glycoside (APG0814) | 0.6 g/L |
| TRIS | 40 Mm |
| Sodium Citrate | 5 g/L |
| Polyoxyethylene (23) Cetyl Ether | 0.5 g/L |
| pH | 7.5 |

Figure 8:
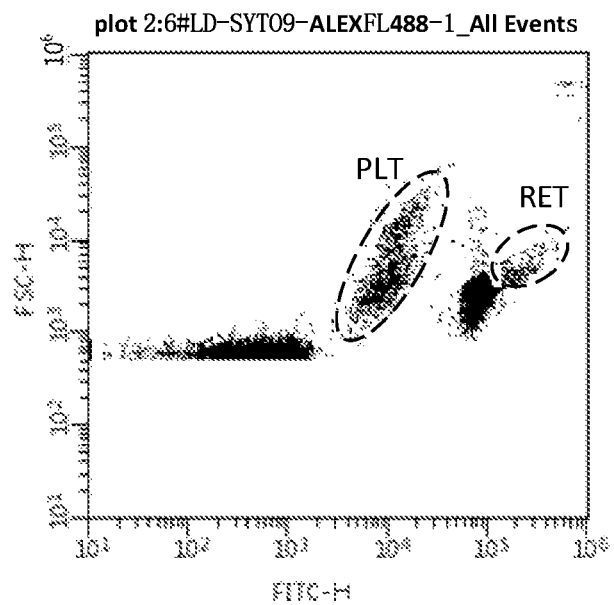
FIG. 8 illustrates a fluorescence-forward scattered light intensity scatter diagram (A) obtained by detecting platelets and reticulocytes by adding a membrane dye and a nucleic acid dye under a deep hemolysis condition, and a fluorescence-side scattered light intensity scatter diagram (B) of white blood cells.
Figure 8:
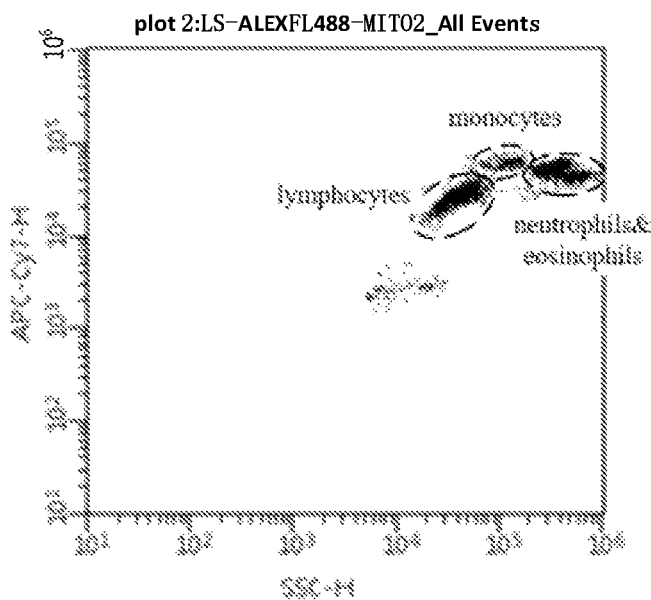

20 μl of a fresh blood sample was added to 1 mL of the solution prepared according to the above-mentioned formula, incubation was performed at 45° C. for 60 seconds, and then detection was performed by adopting a flow cytometer (Mindray BriCyte E6). The excitation wavelength was set as 488 nm, the gain was set as 500, 90° side fluorescence intensity information and 0° forward scattered light intensity information were collected to obtain a two-dimensional cell scatter diagram, as shown in FIG. 8.

As shown in FIG. 8A, two dark particle clusters both consist of lysed red blood cell fragments, and the middle particle cluster consists of platelets, which indicates that platelets can be more significantly differentiated from the red blood cell fragments by this method. The particle cluster at the rightmost side is identified as reticulocytes, therefore information of reticulocytes can be further obtained by this method.

The same treatment was performed on another 20 μl of the same blood sample, and measurement was performed in the same flow cytometer. The excitation wavelength was set as 633 nm, the gain was set as 100,000; and 90° side fluorescence intensity information and 90° side scattered light intensity information were collected to obtain a cell scatter diagram.

As shown in FIG. 8B, the ratios obtained by dividing lymphocytes, monocytes, and neutrophils plus eosinophils were 16.8%, 6.4%, and 76.8%, respectively; while after this sample was tested on the Mindray blood cell analyzer 6800, the ratios of lymphocytes, monocytes, neutrophils and eosinophils were 16%, 5.8%, 78.2% and 1.9%, respectively. The above-mentioned results show that the white blood cell division performed by the above-mentioned method has a relatively good correlation with the ratios obtained by the blood cell analyzer.

Example 9

Verification of Correlation of Platelet Test by Taking Example 1 as Example

Reagent Preparation: Same as Example 1

20 fresh blood samples were provided, and the testing method for each blood sample comprises the steps as follows: adding 20 μl of a fresh blood to 1 mL of the above-mentioned prepared first reagent solution and also adding 20 μl of the second reagent; after performing incubation at 35° C. for 60 seconds, collecting data (the excitation wavelength was 488 nm) by using a flow cytometer (Mindray BriCyte E6); setting the gain as 500; collecting 90-degree side fluorescence signals as fluorescence staining information; and adopting forward scattered light intensity information with a measurement angle of 0 degree. The platelet concentration of the blood sample was calculated by dividing the scatter dots of platelets in combination with the injection volume in the flow cytometer. After the test was ended, the blood samples were tested in a Mindray 6800 instrument, and test values of platelets were recorded. A correlation curve is drawn by using the results obtained by the two testing methods.

Figure 9:
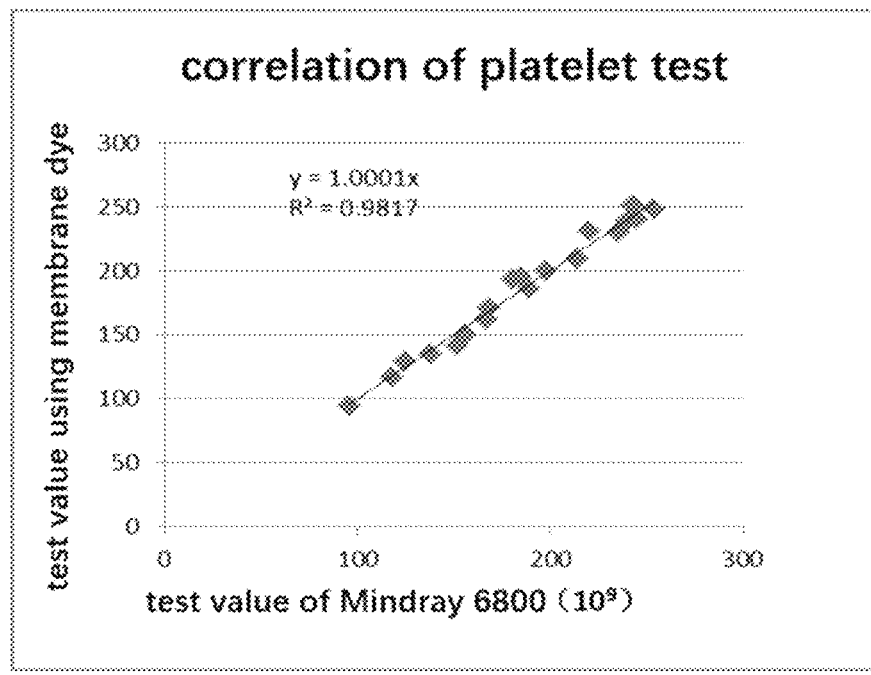
FIG. 9 illustrates the correlation between testing values of the staining method of the present disclosure and testing values of a Mindray 6800 instrument.

It can be seen from FIG. 9 that when the membrane dye Alexa Fluor 488 is used to test platelets, its test values have a relatively good consistency with the test values of the Mindray 6800 instrument, and the correlation coefficient was 0.9817 within a numerical range from 100×109/L to 250×109/L.

The contents described above are only some embodiments of the present disclosure but are not meant to limit the patent scope of the present disclosure. Any equivalent structural modifications based on the description and drawings of the present disclosure, or direct/indirect applications in other related technical fields under the inventive concept of the present disclosure are all included in the patent protection scope of the present disclosure.

The invention claimed is:

1. A method for analyzing a blood sample, comprising:
    treating the blood sample with a first reagent and a second reagent to prepare a test sample, wherein the first reagent is a hemolytic agent that hemolyzes red blood cells in the test sample, and the second reagent is a membrane-specific dye or a mitochondrion-specific dye that stains both platelets and white blood cells in the test sample;
    passing particles in the test sample through a detection area of an optical detection system one by one to obtain scattered light intensity information and fluorescence intensity information of each particle in the test sample;
    differentiating, in a single test channel, the platelets and the white blood cells in the test sample according to the scattered light intensity information and the fluorescence intensity information of each particle in the test sample, wherein the staining by the membrane-specific dye or the mitochondrion-specific dye differentiates the platelets from fragments of the red blood cells produced by the hemolytic agent, the membrane-specific dye is a fluorescence dye capable of specifically staining cell membranes, and the mitochondrion-specific dye is a fluorescence dye capable of specifically staining cell mitochondria; and counting the platelets and classifying the white blood cells according to the scattered light intensity information and the fluorescence intensity information of each particle in the test sample.

2. The method of claim 1, wherein the membrane-specific dye comprises at least one selected from DiA, DiD, DiI, DiO, DiR, DiS, FDA, Alexa Fluor 488, Super Fluor 488 and variant structures using them as parents.

3. The method of claim 2, wherein the membrane-specific dye comprises Alexa Fluor 488 and/or DiD.

4. The method of claim 1, wherein the mitochondrion-specific dye comprises one or more selected from Janus Green B, MitoLite Red, Rhodamine 123, Mitotracker series and variant structures using them as parents.

5. The method of claim 4, wherein the Mitotracker series dye is Mitotracker Red, Mitotracker Green or Mitotracker Red.

6. The method of claim 4, wherein the mitochondrion-specific dye is Rhodamine 123, Mitotracker Deep Red and/or Mitotracker Red.

7. The method of claim 1, wherein the hemolytic agent is used to lyse red blood cells in the blood sample into fragments having light scattering characteristics significantly different from those of platelets.

8. The method of claim 7, wherein the hemolytic agent comprises at least one selected from alkyl glycoside, triterpene saponin, and steroidal saponin.

9. The method of claim 8, wherein the alkyl glycoside is selected from glycoside compounds having the general formula I:

R—(CH2)n-CH3  (1)

wherein R is selected from a group consisting of monosaccharide, deoxy monosaccharide, and polysaccharide formed by two or more monosaccharides selected from the monosaccharide and/or the deoxy monosaccharide, and n is an integer of 5-17.

10. The method of claim 1, wherein the first reagent further comprises:
a nonionic surfactant having the general formula II:

R1-R2-(CH2CH2O)m-H  (II)

wherein R1 is a C8-C23 alkyl group, R2 is —O—, or —COO—, and m is an integer of 10 to 50; and
optionally, at least one organic acid or a salt thereof, wherein the organic acid or the salt thereof is selected from a group consisting of an organic acid having at least one carboxyl group or sulfonic acid group and alkali metal salts thereof.

11. The method of claim 1, wherein the method further comprises counting the white blood cells according to the scattered light intensity information and the fluorescence intensity information of each particle in the test sample.

12. The method of claim 1, wherein the method further comprises classifying or counting immature granulocytes according to the scattered light intensity information and the fluorescence intensity information of each particle in the test sample.

13. The method of claim 1, wherein the method further comprises providing an alarm about reticulocytes according to the scattered light intensity information and the fluorescence intensity information of each particle in the test sample.

14. The method of claim 1, wherein except a first reagent and a second reagent, a third reagent is also used to treat the blood sample, and the third reagent is a nucleic acid dye.

15. The method of claim 14, wherein the method further comprises differentiating or counting reticulocytes according to the scattered light intensity information and the fluorescence intensity information of each particle in the test sample.

16. The method of claim 1, wherein the scattered light intensity information comprises one or two selected from forward scattered light intensity information and side scattered light intensity information.

17. The method of claim 16, wherein the scattered light intensity information is forward scattered light intensity information.

18. The method of claim 1, wherein before treating the blood sample, the method further comprises the steps of obtaining the blood sample, conveying the blood sample to a suitable container and sucking the blood sample from the container; when treating the blood sample, mixing the sucked blood sample with the first reagent and the second reagent; subsequently making particles in the treated blood sample pass through a detection area one by one and irradiating the particles by using a light source, and acquiring fluorescence signals by using a fluorescence detector and acquiring forward scattered light intensity signals and side scattered light intensity signals by using a scattered light detector; dividing a platelet region from a scatter diagram of the fluorescence signals and the forward scattered light intensity signals and acquiring alarming information of reticulocytes; subsequently counting platelets based on the quantity of scatter dots in the platelet region, and dividing a white blood cell region or classifying white blood cells from a scatter diagram of the fluorescence signals and the side scattered light intensity signals, and counting white blood cells or classifying and counting white blood cells based on the quantity of scatter dots in the white blood cell region or a white blood cell classification region;
or, when treating the blood sample, in addition to the first reagent and the second reagent, further mixing the sucked blood sample with a third reagent which is a nucleic acid dye; thus, after detection, further dividing a reticulocyte region on a scatter diagram of the fluorescence signals and the forward scattered light intensity signals; and
subsequently counting reticulocytes based on the quantity of scatter dots in the reticulocyte region.

19. A blood cell analyzer, comprising:
a sampling part comprising a sampler configured to suck a blood sample;
a reaction part comprising a mixing chamber and a reagent supply part, wherein the mixing chamber is in fluid connection with the sampler and the reagent supply part, the mixing chamber is configured to mix the blood sample with a first reagent and a second reagent and perform hemolysis and staining on the blood sample to prepare a treated blood sample to prepare a test sample, the reagent supply part is configured to supply a reagent to the mixing chamber, wherein the first reagent is a hemolytic agent that hemolyzes red blood cells in the test sample and the second reagent is a membrane-specific dye and or a mitochondrion-specific dye that stains both platelets and white blood cells in the test sample;
a detection part comprising a light source, a detection area and at least one optical detector, wherein the light source is configured to align light beams to the detection area that is in fluid communication with the mixing chamber, the detection area is configured for particles in the test sample to pass through one by one, and said at least one optical detector is configured to acquire fluorescence signals, forward scattered light intensity signals and optional side scattered light intensity signals of the particles passing through the detection area; and an analysis part comprising a processor and a non-transitory computer readable storage medium storing a computer program, wherein the processor is operatively connected with the optical detector, and when the computer program is executed by the processor, the processor is caused to generate a scatter diagram of blood cells based on the fluorescence signals and the forward scattered light intensity signals and differentiate and count, in a single test channel, the platelets and the white blood cells in the test sample based on the scatter diagram, wherein the staining by the membrane-specific dye or the mitochondrion-specific dye differentiates the platelets from fragments of the red blood cells produced by the hemolytic agent, the membrane-specific dye is a fluorescence dye capable of specifically staining cell membranes, and the mitochondrion-specific dye is a fluorescence dye capable of specifically staining cell mitochondria.

20. The blood cell analyzer of claim 19, wherein when the computer program is executed by the processor, the processor is further caused to generate a scatter diagram of blood cells based on the fluorescence signals and the forward scattered light intensity signals and to provide an alarm about reticulocytes based on the scatter diagram.

21. The blood cell analyzer of claim 19, wherein when the computer program is executed by the processor, the processor is further caused to generate a scatter diagram of blood cells based on the fluorescence signals and the side scattered light intensity signals, and to differentiate white blood cells and count white blood cells or classify and count white blood cells based on the scatter diagram.

22. The blood cell analyzer of claim 19, wherein the mixing chamber is configured to mix the blood sample with the first reagent, the second reagent and a third reagent, wherein the third reagent is a nucleic acid; and when the computer program is executed by the processor, the processor is further caused to generate a scatter diagram of blood cells based on the fluorescence signals and the forward scattered light intensity signals, and to differentiate and count reticulocytes based on the scatter diagram.

* * * * *